United States Patent [19]

Leasure-Nelson

[11] Patent Number: 5,692,521
[45] Date of Patent: Dec. 2, 1997

[54] SLEEP APNEA RESOLUTION APPLIANCE

[75] Inventor: S. E. Leasure-Nelson, USS Puget Sound (AD38)

[73] Assignee: The United States of America as represented by the Secretary of the Navy, Washington, D.C.

[21] Appl. No.: 598,868

[22] Filed: Feb. 9, 1996

[51] Int. Cl.$^6$ ........................................... A61F 5/56
[52] U.S. Cl. ........................ 128/848; 128/859; 602/902
[58] Field of Search ............................... 128/846, 848, 128/859–862; 602/902; 2/1, 2, 9

[56] References Cited

U.S. PATENT DOCUMENTS

| | | | |
|---|---|---|---|
| 3,429,045 | 2/1969 | Anderson | 128/862 |
| 4,169,473 | 10/1979 | Samelson | 128/848 |
| 4,376,628 | 3/1983 | Aardse | 128/861 |
| 4,470,409 | 9/1984 | Prusmack | 128/862 |
| 5,467,783 | 11/1995 | Meade | 128/848 |

*Primary Examiner*—Michael A. Brown
*Attorney, Agent, or Firm*—Harvey A. Gilbert; William C. Townsend

[57] ABSTRACT

A one piece dental appliance custom molded to a particular patient's dentition for resolution of sleep apnea. The invention features a transpalatal strap extending from one side of the appliance to the opposite side joining the opposing lingual surfaces. The transpalatal strap continuously and uninterruptedly extends between and joins the right and left dental retentive portions of the appliance from one side of the maxillary arch to the opposite side of that arch. The appliance is fabricated from dental acrylic by the dentist in the office and requires a posterior access articulator to adapt acrylic lingually between the maxillary and mandibular casts.

6 Claims, 1 Drawing Sheet

SLEEP APNEA RESOLUTION APPLIANCE

INTRODUCTION

The present invention relates to sleep interruption caused by obstruction of the pharynx, and in particular, provides a means for mechanically managing the condition. The present invention is a medical apparatus, and more particularly, an appliance for treating the medical condition of obstruction sleep apnea, and a process for making said apparatus.

BACKGROUND OF THE INVENTION

Obstructive Sleep Apnea, a temporary stopping of breathing, is a condition characterized by temporary obstruction of the pharynx during sleep and loud snoring caused by such obstruction resulting in partial arousal. Etiological factors are numerous and the effected population is varied. Patients with Obstructive Sleep Apnea Syndrome (OSAS) may exhibit daytime sleepiness and/or fatigue which frequently develops very gradually so that the patient may not be aware of either snoring nor decrease in energy level. Therefore, symptoms may only be realized by interview with bed partner or roommate. These patients are increased risk for accidents, cardiac arrhythmias, pulmonary hypertension and hypercapnia. OSA Syndrome is a potentially lethal disorder. Only a polysomnographic recording permits an accurate diagnosis of an OSA Syndrome.

Treatment for OSAS has been attempted by medical and surgical means and by use of various positional or electrical devices. Both medical and surgical means are invasive, typically irreversible and therefore frequently unacceptable to the patient. Additionally, neither medical nor surgical means enjoy complete success. Electrical devices at worst cause pain due to the amount of current required to stimulate muscular contraction and at best are complex and expensive including electric generators and monitors.

Some positional devices previously described have limited value in the treatment of OSAS because they restrict or occlude the airway, others require specialized equipment, materials or use of a dental laboratory technician, still others are uncomfortable or unduly fragile and could pose threat of aspiration. An example of prior art is disclosed in U.S. Pat. No. 5,267,862 by Parker.

SUMMARY OF THE INVENTION

It is thus an object of the present invention to provide a non-invasive means for the treating and managing obstructive sleep apnea.

It is yet an another object of the present invention to provide a non-surgical means for treating and managing obstructive sleep apnea.

It is still another object of the present invention to provide a non-restricting and non-occluding means for treating and managing obstructive sleep apnea.

It is further another means for providing a comfortable, easily fabricated and non-fragile means for treating and managing obstructive sleep apnea.

It is finally another object of the present invention to provide an effective, completely reversible, comfortable treatment for management of OSAS.

It is safer, more durable, more hygienically maintainable, less expensive than prior art and can be fabricated fully by a general dentist with materials commonly found in any dental clinic. The appliance consists of a custom-made acrylic positional device formed on diagnostic casts using pre-determined prognathic (mandible forward) position accurately recorded with impression material.

The single material fabrication of this appliance provides simplicity, durability, cleansibility due to uniform density, safety and economy. The described configuration provides a comfortable and effective management of Obstructive Sleep Apnea Syndrome.

DETAILED DESCRIPTION OF THE INVENTION

Figure 1:
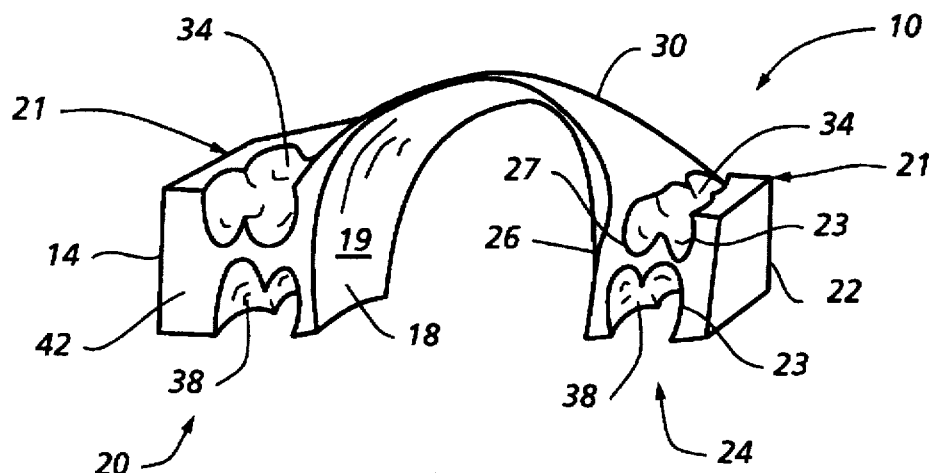
FIG. 1 is a posterior perspective view of the appliance of the present invention.

With reference to FIG. 1, a perspective posterior view of a completed appliance constituting the present invention is shown. Since each device is custom-made, each will have it's own unique contour relative to the patient's oral anatomy.

The sleep apnea appliance 10 is shown in FIG. 1 consisting of the left buccal adaptation 14 and the left lingual adaptation 18 which are part of the left dental retentive portion 20, and the right buccal adaptation 22 and the right lingual adaptation 26 which are part of the right dental retentive portion 24. The transpalatal strap 30 extends continuously and uninterruptedly in the shape of a palatal arch from the left lingual adaptation 18 to the right lingual adaptation 26. The maxillary dentition attachment 34 and the mandibular dentition attachment 38 are molded into the left dental retentive portion 20 and the right dental retentive portion 24 to the extent of accommodating at least three teeth in each attachment position 34 and 38 of the appliance 10. On each side of the appliance 10, the outer portion of the right dental retentive portion 24 and the left dental retentive portion 20 provides the finger grips 25 and 21, respectfully.

Accurate plaster casts are made of the patient's upper arch and lower arch. A bite registration is made with the mandible protruded maximally, based on the patient's comfort, usually 4–10 mm, and open 5–10 mm, again based on the patient's comfort. A position which causes tension or discomfort during the bite registration phase may be too far forward and must be adjusted since this position will be maintained during hours of sleep. This position when maintained via the appliance 10 will lift the tongue away from the soft plate and posterior pharynx allowing a patent airway during hours of sleep thus relieving the obstructive apnea. Cusp tip to cusp tip protrusive relationships should be avoided. If a cusp tip to cusp tip recording is optimal for the patient, the interarch space is increased to ensure adequate strength of bulk in acrylic. All areas of the device 10 must be at least 3 mm thick for strength.

Figure 2:
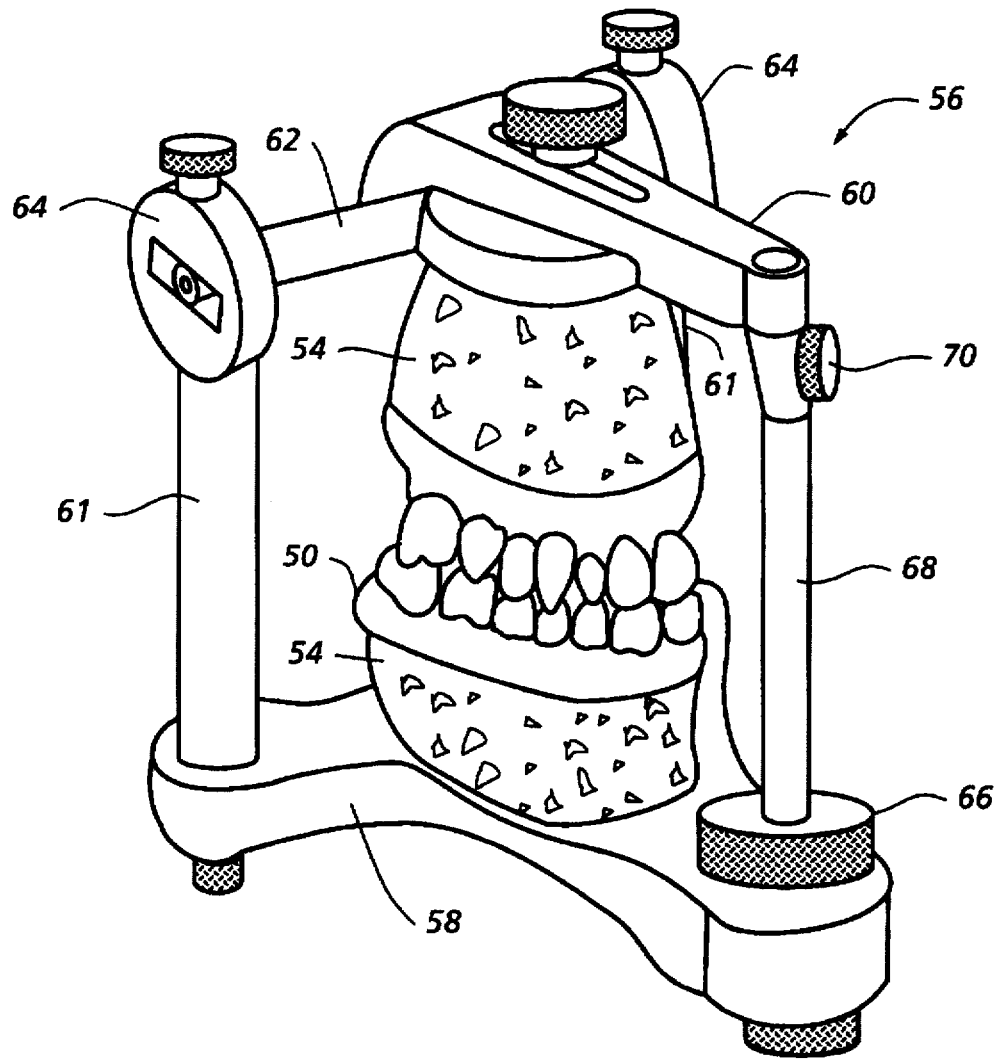
FIG. 2 is a front perspective view of an articulator for preparation of the present invention.

The maxillary cast 46 and the mandibular cast 50 are mounted on an articulator 56, as shown in FIG. 2, a device used to simulate the relationship of maxillary to mandibular teeth, with posterior access to lingual structures. Most semi-adjustable articulators would serve for this purpose. Posterior access is required to ensure proper adaptation of lingually placed acrylic. The articulator 56 shown in FIG. 2 provides the required posterior access for preparation of the appliance 10. It is of a type commonly known to those skilled in the art. The articulator 56 has a base support 58 and upper support 60 for mounting the mandibular cast 50 via the plaster portion 54 and the maxillary cast 46 via the plaster portion 54, respectively. The vertical posts 61 extend from the base support 58 to hinges 64 which permit rotation and lateral front to back movement of the shaft 62 which connects to the upper support 60 through the shaft 62. The incisal stop pin 68 controls the upward and downward rotational motion of the upper support 60 about the shaft 62 to position the maxillary cast 46 relative to the mandibular cast 50. The lock screw 70 is used to fix the positions of the casts 46 and 50 so that the appliance 10 can be fabricated to the specification for the particular patient. Once mounted, the maxillary and mandibular teeth are not in contact. Casts are marked with colored pencil to show proper extension of acrylic indicating the design of the device. The appliance 10 includes the buccal and lingual crests of contour 15, 19, 23, and 27 in FIG. 1 of a minimum of three teeth per quadrant opposing maxillary and mandibular. The appliance 10 includes a continuous transpalatal strap 30, of acrylic to provide rigidity and bulk and does not include coverage of the incisors thereby maximizing the airway.

Critical areas of each cast are coated with separating medium. Clear acrylic is prepared by sifting polymer into monomer with preferably little or no stirring. This method will minimize air bubbles incorporated, increase density, and therefore improve durability and cleansibility of the device. When the acrylic is doughy, it is adapted onto the cast palate and those maxillary teeth included in the design both buccally, and lingually with the articulator 56 open. Adaptation is facilitated by fashioning acrylic into a rope shape prior to adaptation. Additional doughy acrylic is placed over involved mandibular teeth and adapted to buccal, and lingual surfaces with the articulator 56 open. Monomer is added to occlusal surfaces of the adapted acrylic while it is still soft to facilitate union of the acrylic between the casts' teeth.

The articulator 56 is closed and secured in this closed position with rubber bands to control expansion of the acrylic during polymerization. The articulator 56 is then inverted. The acrylic is continuously adapted until it begins to give off heat. Lingual adaptation is from the posterior of the articulator 56 between the vertical posts 61. Polymerization is completed with the articulator inverted to facilitate palatal adaptation. Sufficient facial thickness of acrylic is left to allow the patient to place and remove the device by engaging the edge of left and right finger grips 20 and 24, respectively, with finger or thumb tips. Three (3) millimeters is normally adequate for this purpose.

The plaster maxillary and mandibular casts 46 and 50 will be destroyed in the process of removing the appliance 10 for finishing. The plaster teeth are cut away from the casts to release the appliance 10. The non-tissue surface is smoothed and acrylic reduced to design markings and desired thickness of 3 mm minimum. Anterior and posterior edges of the transpalatal strap 30 are thinned to be as unobtrusive and comfortable as possible. The internal surfaces where the plaster teeth have made maxillary and mandibular dentition attachments 34 and 38 are evaluated for excess undercut. The appliance 10 is made retentive enough to ensure against dislodgement during the patient's unconscious hours, large enough to prohibit swallowing or aspiration possibilities and rigid enough to position the mandible forward independent of the patient's unconscious behavior. These factors will vary due to the custom nature of the device.

The appliance 10 is expected to go into place snugly and be removable with finger pressure. Final adjustment of retention is made at time of delivery by selective reduction of effective undercut on the tissue surface at maxillary and mandibular dentition attachments 34 and 38 of the appliance 10. The delivered appliance 10 is comfortable and passive. The device is for limited wear only and is not worn for more than eight hours per day at hours of sleep. If extended hours of wear are required for the health of the patient, a full arch appliance must be used to prohibit super eruption of the teeth.

The structure and method disclosed herein illustrate the principles of the present invention. The invention may be embodied in other specific forms without departing from its spirit or essential characteristics. The embodiment of the invention described herein is to be considered in all respects as exemplary and illustrative rather than restrictive. Therefore, the appended claims rather than the foregoing description define the scope of the invention. All modifications to the embodiment described herein that come within the meaning and range of equivalence of the claims are embraced within the scope of the invention.

What I now claim as my invention is:

1. The method of fabricating a dental appliance for resolving sleep apnea, said appliance being one-piece and having maxillary and mandibular dentition attachments joined by a transpalatal strap, said method comprising the steps of:

(a) preparing accurate casts of the patient's upper and lower arches;

(b) making a bite registration with the mandible protruding maximally, based on the patient's comfort, from about four (4) millimeters to about ten (10) millimeters, and open from about five (5) millimeters to about ten (10) millimeters, based on the patient's comfort;

(c) mounting said plaster casts on an articulator having posterior access to lingual structures;

(d) marking said mounted plaster casts with colored pencil or equivalent to note proper extension of acrylic to be introduced to fabricate said appliance;

(e) coating said plaster casts with separating medium so that the buccal and lingual crests of contour of a minimum of three (3) teeth per quadrant opposing maxillary and mandibular are so coated and excluding the incisors to maintain maximum airway;

(f) preparing clear acrylic by sifting polymer into monomer with little or no stirring to minimize the inclusion of air bubbles and increasing the mixture density until said acrylic is doughy;

(g) adapting said acrylic onto said plaster casts in the areas coated with separating medium including the coated maxillary teeth, the coated mandibular teeth and involved buccal and lingual surfaces;

(h) adding monomer to the occlusal surfaces of the adapted acrylic while it is still soft to facilitate union of the acrylic between the teeth of the casts;

(i) closing and securing the articulator in the closed position with rubber bands to control expansion of the acrylic during polymerization;

(j) inverting the articulator to facilitate palatal adaptation to produce a palatal strap during completion of polymerization;

(k) maintaining sufficient facial thickness of acrylic, usually about to three (3) millimeters, to allow the patient to place and remove the appliance by engaging a buccal portion with finger or thumb tips;

(l) removing the plaster casts from the articulator and from the appliance;

(m) smoothing the non-tissue surface and reducing the acrylic to the colored pencil markings; and (n) thinning the anterior and posterior edges of the palatal strap to be as unobtrusive and comfortable as possible.

2. The method of claim 1 wherein said articulator is of the semi-adjustable type for lingual access.

3. The method of claim 1 wherein said adaptation is facilitated by fashioning said acrylic into a rope shape.

4. A dental appliance for treating sleep apnea by immobilizing the maxillary and mandibular dental structures relative to each other and relative to the palate and airway through the dental structures, comprising:

means for providing dental retention of the left maxillary and mandibular dental structures;

means for providing dental retention of the right maxillary and mandibular dental structures; and palatal arch-shaped means for continuous and uninterrupted joinder of said left and right means for providing dental retention, said shaped means extending between said dental means, in juxtaposition with said palatal arch, and providing a maintainable airway between said means for joinder and said mandibular structure.

5. The appliance of claim 4 wherein said means for joinder is a transpalatal strap.

6. A dental appliance for the treatment of sleep apnea, comprising:

a left dental retentive portion;

a right dental retentive portion; and a continuous transpalatal strap extending between and joining said left and right dental retentive portions from one side of the maxillary arch to the opposite side of said arch.

\* \* \* \* \*